(12) United States Patent
Koske (10) Patent No.: US 7,887,592 B2
(45) Date of Patent: Feb. 15, 2011

(54) PROSTHETIC INTERVERTEBRAL DISCS ASSEMBLIES HAVING COMPRESSIBLE CORE ELEMENTS WITH ENHANCED TORQUE TRANSMISSION

(75) Inventor: Nicholas C. Koske, San Jose, CA (US)

(73) Assignee: Spinal Kinetics, Inc., Sunnyvale, CA (US)

( * ) Notice: Subject to any disclaimer, the term of this patent is extended or adjusted under 35 U.S.C. 154(b) by 704 days.

(21) Appl. No.: 11/674,686

(22) Filed: Feb. 14, 2007

(65) Prior Publication Data

US 2008/0195206 A1 Aug. 14, 2008

(51) Int. Cl.
*A61F 2/44* (2006.01)

(52) U.S. Cl. ............... 623/17.15; 623/17.11; 623/17.16

(58) Field of Classification Search .... 623/17.11–17.16
See application file for complete search history.

(56) References Cited

U.S. PATENT DOCUMENTS

| | | | |
|---|---|---|---|
| 6,579,320 B1 * | 6/2003 | Gauchet et al. .......... | 623/17.15 |
| 6,626,943 B2 * | 9/2003 | Eberlein et al. .......... | 623/17.15 |
| 7,270,680 B2 * | 9/2007 | Ralph et al. .............. | 623/17.14 |
| 7,563,286 B2 * | 7/2009 | Gerber et al. ............ | 623/17.14 |
| 2006/0111783 A1 * | 5/2006 | Aflatoon et al. .......... | 623/17.14 |
| 2006/0276900 A1 * | 12/2006 | Carpenter ................ | 623/17.15 |
| 2007/0032874 A1 * | 2/2007 | Lee et al. ................. | 623/17.13 |
| 2007/0032875 A1 * | 2/2007 | Blacklock et al. ........ | 623/17.15 |
| 2007/0239279 A1 * | 10/2007 | Francis .................... | 623/17.16 |
| 2008/0077244 A1 * | 3/2008 | Robinson ................. | 623/17.16 |
| 2008/0288077 A1 * | 11/2008 | Reo et al. ................. | 623/17.16 |

* cited by examiner

*Primary Examiner*—Thomas C Barrett
*Assistant Examiner*—Christine L Nelson
(74) *Attorney, Agent, or Firm*—Orrick, Herrington & Sutcliffe LLP (57) ABSTRACT

This description deals with a medical device, specifically a prosthetic intervertebral disc having a compressible core that is mechanically interactive with the prosthetic disc's end plates thereby providing excellent torque or twisting transmission between the end plates.

22 Claims, 10 Drawing Sheets

Fig. 38b

PROSTHETIC INTERVERTEBRAL DISCS ASSEMBLIES HAVING COMPRESSIBLE CORE ELEMENTS WITH ENHANCED TORQUE TRANSMISSION

FIELD

This description deals with a medical device, specifically a prosthetic intervertebral disc having a compressible core that is mechanically interactive with the prosthetic disc's end plates thereby providing excellent torque or twisting transmission between the end plates.

BACKGROUND

The intervertebral disc is an anatomically and functionally complex joint. The native intervertebral disc is made up of three component structures: (1) the nucleus pulposus; (2) the annulus fibrosus; and (3) the vertebral end plates. The biomedical composition and anatomical arrangements within these component structures are related to the biomechanical function of the disc.

The spinal disc may be displaced or damaged due to trauma or a disease process. As a result of such displacement or damage, the nucleus pulposus may herniate and protrude into the vertebral canal or intervertebral foramen. That deformation is commonly known as a herniated or "slipped" disc. The deformation may press upon one or more of the spinal nerves exiting the vertebral canal through the partially obstructed foramen, causing pain or paralysis in its area of influence.

One method of alleviating this condition involves surgically removing the involved disc and fusing the two adjacent vertebrae. In this procedure, the removed disc is replaced by a spacer and secured to the neighboring vertebrae by screws, plates, and rods. Although "spinal fusion" evidences excellent short-term results, long-term studies show that the procedure eventually leads to degenerative changes in the spine, particularly at adjacent mobile segments. As a result of the fused segment's increased stiffness, adjacent discs incur increased motion and stress. In the long term, this change in the mechanics of the spine causes the adjacent discs to degenerate.

Prosthetic intervertebral discs are now used as alternatives to spinal fusion. Various artificial intervertebral disc designs are extant; many share the goal of mimicking the kinematics and load-sharing properties of the natural intervertebral disc. Two such design categories are ball-and-socket joint type discs and elastic rubber type discs.

Artificial discs of the ball-and-socket type usually include a pair of concave metal plates, one to be attached to the upper vertebra and the other to be attached to the lower vertebra, and a rounded core working as a ball. The concavities within the metal plates cooperate with and rotate with respect to the rounded core. The ball-and-socket type disc allows free rotation between the adjacent vertebrae between which the disc is installed. Such discs do not share any of the toad placed on the spine as the spine bends.

In contrast, ball-and-socket discs have very high stiffness in the vertical (or compressive) direction, much higher than the normal compressive stiffness of the natural disc. As a result, although these discs allow flexion of the spine where a fused disc does not, the structure of these discs still causes adjacent discs to absorb extra compressive loads and still allow eventual and early degeneration of those discs.

Another common artificial disc design includes an elastic rubber or elastomeric polymer body embedded between a pair of metal plates. The disc is introduced into the emptied region between two adjacent vertebrae by affixing the two metal plates, via a surgical procedure, to those two vertebrae. The elastomeric polymer body is bonded to the metal plates through a rough porous interface surface. This disc design is able both to absorb vertical, compressive shocks and to bear loads in that direction. However, the interface between the elastomeric polymer body and the metal plates is subject to peeling or severance due to the nature of the junction.

Described here are prosthetic discs or prosthetic disc subassemblies having a compressible core member that interlocks with the endplates to provide torque transmission between the endplates.

SUMMARY

This description includes prosthetic intervertebral disc assemblies or prosthetic intervertebral disc assemblies subassemblies. The prosthetic discs include an upper end plate, a lower end plate, and a compressible core member situated between the two end plates. The compressible core member interacts, directly or indirectly, with the end plates via protrusions from the compressible core member. The protrusions extend into openings in the end plates or in intermediate members, such as springs, forming part of the endplates. The disc may also include stress members and components to affix the prosthetic disc to vertebral bone.

BRIEF DESCRIPTION OF THE DRAWINGS

The Figures are not necessarily drawn to scale. Some components and features may he exaggerated for clarity.

DESCRIPTION

The described device comprises a prosthetic intervertebral disc assembly suitable for use in the replacement of a natural spinal disc or comprises a subcomponent of a prosthetic spinal disc. In particular, this described device comprises a compressible core or core assembly that physically interlocks, directly or indirectly, with the tipper and lower end plates. The upper and lower end plates are configured to rotate, in turn axially with respect to each other. Further, the upper and lower end plates are configured to be affixed to adjacent spinal vertebrae and two rigidly rotate with those vertebrae to which they are fixedly attached.

By "interlock" we mean that the compressible core or core assembly includes at least one projection that, directly or indirectly, extends into each of the two end plates such that axial twisting of the core or core assembly transmits of force into the end plates through the core projection or projections.

The relationship between axial torsional or twisting forces applied to the core and the resulting force applied to the end plates may be linear, proportional, nonlinear, or reflect a hysteresis upon twisting and unwinding.

The described prosthetic disc may further comprise tension members or components apart from or integrated with the compressible core assembly or core member, that tend to provide responsive movement between the opposing end plates variously in flexion—extension, side to side movement, and axial motion. Our prosthetic disc subcomponent may, for instance, comprise less than all of an operative disc but, in any case, may be assembled into an operable prosthetic disc with the addition of specified functional components or specified physical components.

Components suitable for providing movement in flexion-extension and side to side or separately discussed in may be included independently as needed or desired in a complete prosthetic disc.

Additionally, components (independent or integrated) that may be attached to or included with the prosthetic disc and configured to affix the end plates (directly or indirectly) to adjacent vertebrae are separately discussed below.

Figure 1:
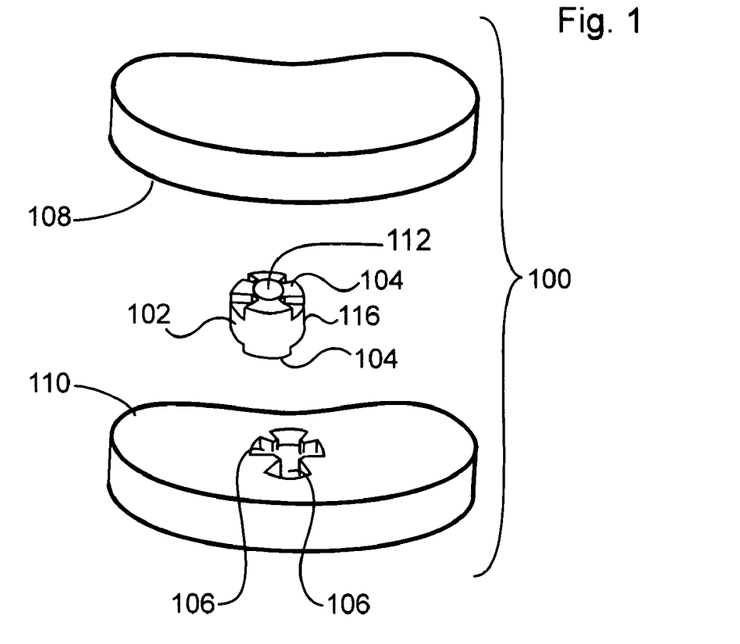
FIG. 1 provides exploded view of a first variation of our prosthetic disc.

FIG. 1 shows and exploded perspective view of a first variation of our prosthetic disc (100) comprising a compressible core (102) having a number of protrusions (104) that extend into corresponding openings or depressions (106) in upper end plate (108) and lower end plate (110). The protrusions (104) are shown as having, substantially straight, radial extending sides. The compressible core (102) is shown having a central plug-like extension (112) that serves principally to provide a measure a centering of the core (102) during side to side and front to back motion of the disc.

Figure 2:
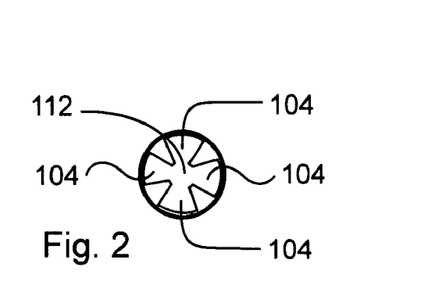
FIG. 2 shows a top view of the core clement of the disc shown in FIG. 1.

FIG. 2 provides a top view of disc element (102) having multiple protrusions or protuberances (104) and the central plug-like extension (112). Although the disc (102) is depicted as being substantially round, the disc (102) need not be so. Depending upon the choice and placement of any tension imparting elements, the disc (102) may be configured, for instance, to assist in providing additional resistance to movement in flexion—extension side to side, and twisting movements. To accomplish such a goal, the overall shape of the disc clement (102) may be an oval form with the major axis of the oval being situated on the linear axis of moment for which additional resistance is desired. The composition of the disc (102) may also be varied, for instance, to include materials of differing hardness is in different parts of the disc element (102). A discussion of materials suitable for use in the disc element (102) may be found below.

Figure 3:
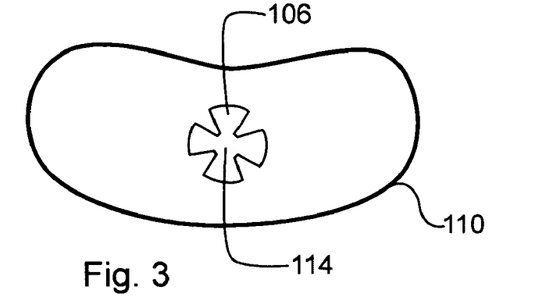
FIG. 3 shows a top view of an end plate of the: disc as shown in FIG. 1
Figure 4:
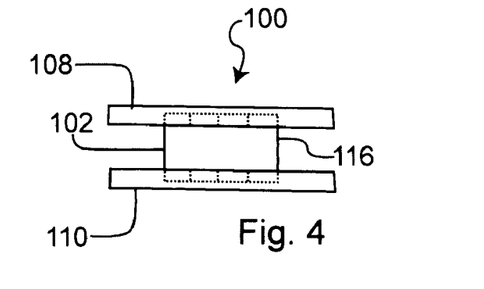
FIG. 4 provides a side view of the disc shown in FIG. 1 as assembled.

FIG. 3 provides a top view of a lower end plate (110) showing the various openings (106, 114) into which the projections (104, 112) of the disc element (102) may be placed. In this variation of the device, only the projections (104) extend into the end plates (110, 108). See also FIG. 4, where a front view of the assembled prosthetic disc (100) may be found. The disc (100) may also be configured so that the projections (104) extended through the end plate or plates (108, 110). The portion of the disc element not forming the projections, i.e., the disc body (116), may also extend into the end plate or plates (108, 110).

Figure 5:
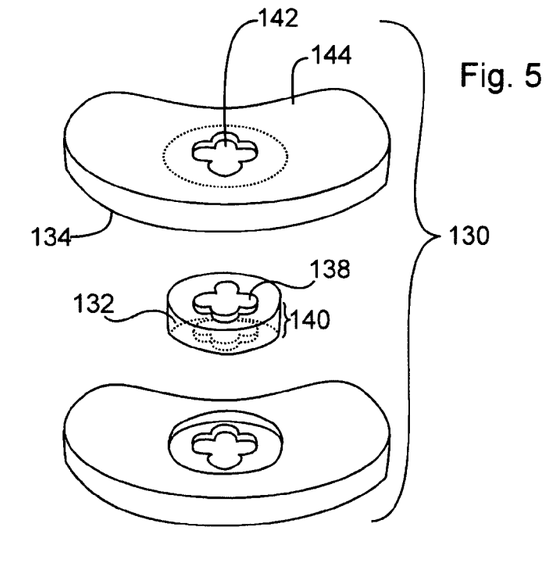
FIG. 5 provides an exploded view of another variation of our prosthetic disc.

FIG. 5 shows an exploded view of another variation of our prosthetic disc (130). This variation includes a compressible core element (132), an upper end plate (134), and a lower end plate (136).

In this variation, the core element (132) includes protrusions (138) on both the lower and upper ends of the compressible core element (132) and includes a core body (140). The projections (138) extend through openings (142) in the opposing sides (144) of upper and lower end plates (134, 136). A portion of the core body (140) extends into the relief openings (146) found in each to the upper and lower end plates (134, 136). As is the case with the other described variations, any twisting force imparted upon the core (132) will be transferred to the end plates (134, 136) due to the physical interaction between the projections or protruberances (138) and corresponding openings (142).

Figure 6:
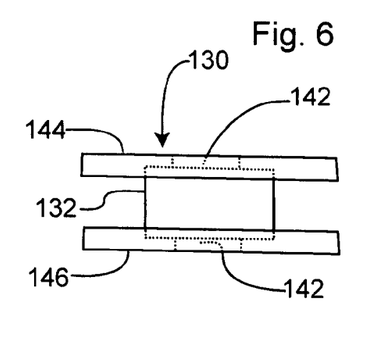
FIG. 6 provides a side view of the disc shown in FIG. 5 as assembled.

FIG. 6 is a front view of the disc assembly (130) showing projections (142) extending through upper and lower end plates (134, 136).

Figure 7:
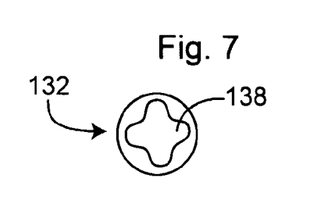
FIG. 7 shows a top view of one variation of a core element suitable for use in the disc variation shown in FIG. 5.

FIG. 7 shows a top view of compressible core member (132) and its projections (138). The core (132) in this instance has an overall, substantially round shape.

Figure 8:
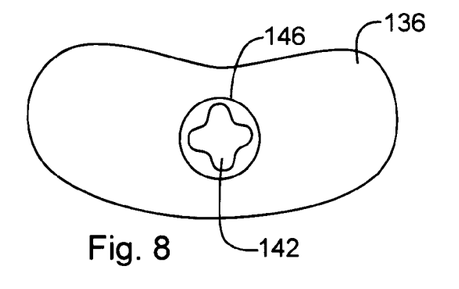
FIG. 8 shows a top view of an end plate of the disc shown in FIG. 5 configured for use with a core element shown in FIG. 7.

FIG. 8 shows a top view of a lower end plate (136) with through-opening (142) and relief opening (146). The relief opening (146) is shallow and does not extend through the end plate (136). In this variation, a bottom view of tipper end plate (134) would be identical to the view of lower end plate (136) found in FIG. 8. In any case, the relief opening (146) is substantially round to match the outside shape of core element (136).

Figure 9:
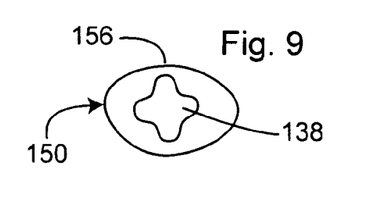
FIG. 9 shows another variation of core element suitable for use in the disc variation shown in FIG. 5.
Figure 10:
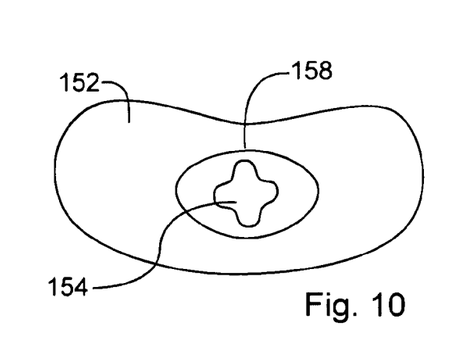
FIG. 10 shows atop view of an end plate of the disc shown in FIG. 5 configured for use with the core element shown in FIG. 9.

FIGS. 9 and 10 show, respectively, an alternative shape for compressible core (150) and matching openings in end plate (152).

FIG. 9 shows a core (150) heading a generally oval outside shape. The projection (138) is configured for placement within the opening (154) in the end plate (152). The exterior oval shape (156) of the compressible core member (150) may be used in any of several different ways. In one variation, as shown in FIG. 10, the depression or opening (158) in the end plate (152) may be formed to be the same shape and size as that of the exterior oval-shaped (156) of core member (150).

Figure 11:
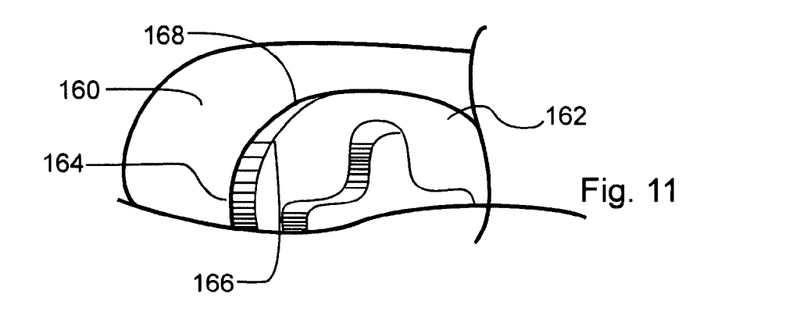
FIG. 11 shows a top view of a suitable fitting for the core element shown in FIG. 9 in the endplate shown in FIG. 10.

Another variation of the oval care is shown in FIG. 11. FIG. 11 is a partial top view of an end plate (160) with an oval core member (162) and placed. The outer opening (164) in end plate (162) is specially shaped and oversized in comparison to the exterior oval shape (166) of core member (162). A progressively opening gap (168) may be seen between the exterior oval shape (166) and the outer opening (164). The depicted gap (168) permits the core component (162) to twist but provides a progressively increasing resistance to such twisting as the gap (168) closes or collapses during the twisting. The size and shape of gap (168) may be chosen to provide a variety of relationships between the twisting force and the resulting resistance.

Figures 12, 13A:
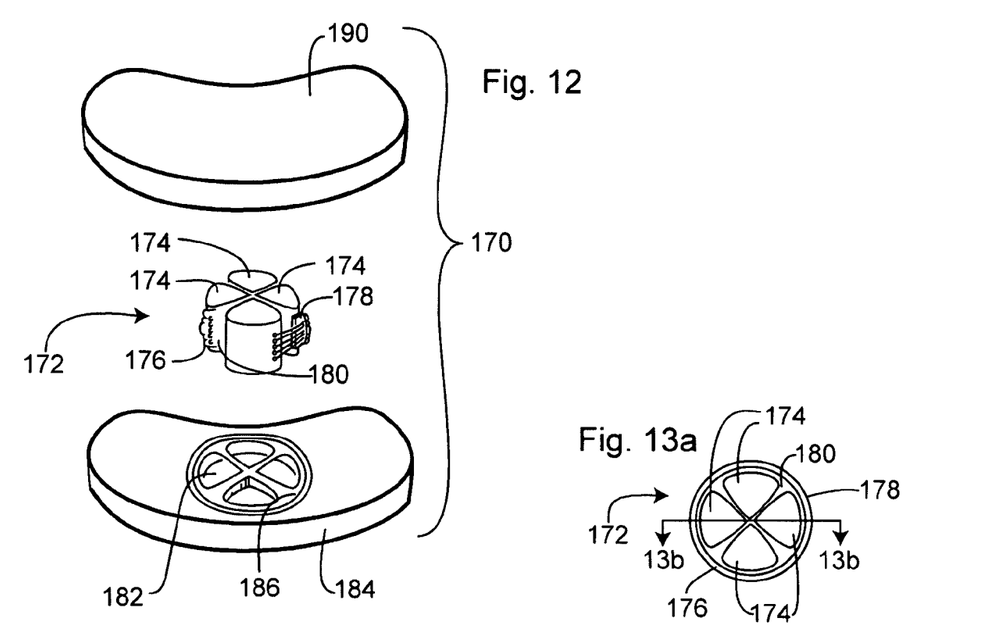
FIG. 12 shows exploded view of another variation of our prosthetic disc.
FIG. 13A shows a top view of the core assembly for use in the disc assembly shown in FIG. 12.

FIG. 12 shows an exploded perspective view of another variation of our prosthetic disc (170). In this instance, the core assembly (172) comprises an assemblage of a multiplicity of core segments (174) surrounded by a filamentary member (176) wrapped around the assemblage of core segments (174) and further surrounded by a bellows member (178). The core assembly (172) may further comprise a filler material (180). The core segments (174) extend into the con-elating openings (182) in the end plate (184) to provide the resistance to twisting forces discussed elsewhere. The end plate (184) also includes the receiving slot (186) for tie bellows (178).

In this variation, the core segments (174) may be compressible and comprise an elastic, elastomeric, or otherwise rubbery material such as a silicone, a thermoplastic elastomer (TPE), or other similar material. Other suitable materials are discussed elsewhere herein. A filler (180) may be a compatible, typically castable, elastomeric material a similar (or different) physical parameters allowing the tailoring of the overall compression/rebound characteristics of the completely assembled core assembly (172) aid, therefore, the prosthetic disc (180) itself. For instance, the core segments (174) may comprise a TPE with a compressibility of 737 N/mm +/−885 N/mm. Such an arrangement would provide a biologically similar compressibility and yet provide damping an enhanced shock absorption as compared to a core comprising only the single, higher-compressibility TPE.

Additionally, each of the core members and the core assemblies may be a composite assembly of an outer or enclosing elastic elastomeric, or otherwise rubbery material surrounding another material such as a suitable liquid, gel, or hydrogel.

Most suitable as such included materials are hydrogels. Hydrogels are water-swellable or water-swollen polymeric materials typically having structures defined either by a crosslinked or an interpenetrating network of hydrophilic homopolymers or copolymers. In the case of physical crosslinking, the linkages may take the form of entanglements, crystallites, or hydrogen-bonded structures to provide structure and physical integrity to the polymeric network.

Suitable hydrogels may be formulated from a variety of hydrophilic polymers and copolymers including polyvinyl alcohol, polyethylene glycol, polyvinyl pyrrolidone, polyethylene oxide, polyacrylamide, polyurethane, polyethylene oxide-based polyurethane, and polyhydroxyethyl methacrylate, and copolymers and mixtures of the foregoing.

Silicone-base hydrogels are also suitable. Silicone hydrogels may be prepared: by polymerizing a mixture of monomers including at least one silicone-containing monomer and or oligomer and at least one hydrophilic co-monomer such as N-vinyl pyrrolidone (NVP), N-vinylacetamide, N-vinyl-N-methyl acetamide, N-vinyl-N-ethyl acetamide, N-vinylformamide, N-vinyl-N-ethyl formamide, N-vinylformamide, 2-hydroxyethyl-vinyl carbonate, and 2-hydroxyethyl-vinyl carbamate (beta-alanine).

The core assembly (172) in this variation may further comprise a fiber wrapping (176). One suitable method for producing such a wrapping (176) is via the simple step of winding one or more fibers around the periphery of assembly (172) in the mid-region of the core assembly, that region of the core assembly (172) that would be exposed when the core segments (174) are inserted into the end plates (184, 190). The fiber wrapping (176) may have the functions of maintaining the integrity and shape of the core assembly (172) or may have the additional function (by providing tension or preloading into the fibers during winding) of adding an amount of bulk compressibility to the core assembly (172).

Suitable materials for the fiber range from high tensile strength wire comprising various stainless steels and super-elastic alloys (such as nitinol) to polymeric fibers comprising polyolefins such as polyethylene, polypropylene, low-density and high density polyethylenes, linear low-density polyethylene, polybutene, and mixtures and alloys of these polymers. HDPE is especially suitable. Other suitable materials for preparing the various fibers include polyamides (e.g., various of the Nylons), other polyesters such as polyethyleneterephthalate ("PET" commercially available as DACRON and HYTREL), as well as liquid crystal polymers such as those available under the tradename VECTRA, polyfluorocarbons such as polytetrafluoroethylene and e-PTFE. Other nonpolymeric materials such as carbon fiber and glass fiber. The fibrous components may be single strands or, more typically, multi-strand assemblages. As a matter of design choice, the fibers would generally have a high modulus of elasticity and possess high wear resistance. The fibers may have a modulus of elasticity such as at least about 100 MPa, perhaps at least about 500 MPa. The fibers may have a diameter that ranges front about 0.1 to about 5 mm, such as about 0.2 mm to about 2 mm.

The bellows (178) may also have a variety of functions. It may serve as a shield to protect the materials of the core assembly (172) found in its interior. Additionally, it may provide resistance to the movement of the disc assembly (170) to various forces (flexion-extension, side to side, and axial twisting). The bellows (178) may comprise metals or alloys, e.g., superelastic alloys such as nitinol or stainless steels, or appropriate polymeric materials, e.g., the polyolefins and polyfluorocarbons, polyetheretherketone, and the like.

The bellows (178) may fit into the groove (186) and, if necessary for the desired function of the bellows, adhere to the groove (186). The bellows may mechanically adhered to the end plates using, e.g., an interference ring. It may be welded, soldered, or glued to the end plates.

The end plates (190, 184) of this variation and the other variations discussed herein may comprise such biologically acceptable materials as titanium, titanium alloys (e.g. with aluminum or tungsten or the like), stainless steels, certain ceramics, and certain polymers (engineering plastics, filled polymers, or reinforced polymers). One particularly suitable material is a widely known titanium alloy (Titanium—6% of Aluminum—4% of Vanadium (Ti6Al-4V)). This titanium alloy has been a material of choice for medical implants particularly orthopedic implants for decades. This alloy is generally considered chemically inert, compatible with human tissue, and resistant to corrosion by human body fluids.

We have also had good experience with coating at least the bone contact areas of our device with a titanium plasma spray to increase bone-contact surface area. The titanium spray material comprises commercially pure titanium. Other materials may be suitable for increasing the surface area of the bone contact areas.

Selected castable, biocompatible epoxies (two-part, one-part, or ultraviolet-light curable) are also suitable for end plates. Such epoxies are commercially available from Ciba Specialty Chemicals (Basel, Switzerland), Master Bond. Inc. (Hackensack, N.J.), and others. Other castable polymers are also suitable, including certain polyurethanes, polyesters, and polyacrylics. Implant grade polyurethanes such as those commercially available from the Polymer Technology Group or Cardiotech are suitable in some of our variations.

Generically, when we speak broadly of such polymers, we include in the material referred to, such adjuvants or modifiers as fillers (minerals, polymeric fibers, metal or alloy powders such as silver for conductivity or tantalum or tungsten for radio-opacity), thickeners, thinners accelerators, adhesion promoters, flexibilizers, wetting agents, etc.). Medicinal adjuvants such as bone-growth enhancers, antibiotics, etc. are also in that class of materials considered as integrated into the generic polymer class in those components where the medicinal function is desired.

Figure 13B:
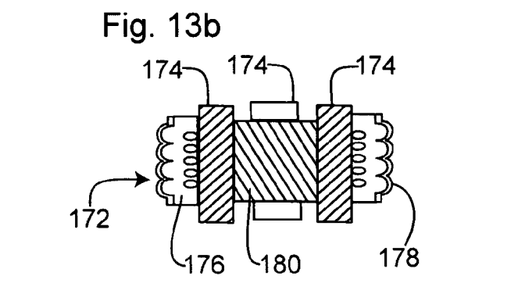
FIG. 13B shows a side view, cross-section of the core assembly shown in FIG. 13A.

FIG. 13A shows a top view of core assembly (172) arid its component core segments (174) surrounded by filler (180). The fiber winding layer (176) and the outer bellows member (178) may also be seen in this view. FIG. 13B similarly shows a side view, but a cross section in this instance, of core assembly (172) and depicts more clearly the placement of filler 180) with respect to core segments (174).

Figure 14:
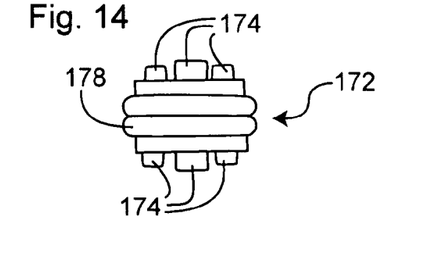
FIG. 14 shows a side view of the core assembly shown in FIGS. 13A and 13B.

FIG. 14 provides a side view of core assembly (172). The bellows member (178) may be clearly seen in this view.

Figure 15A:
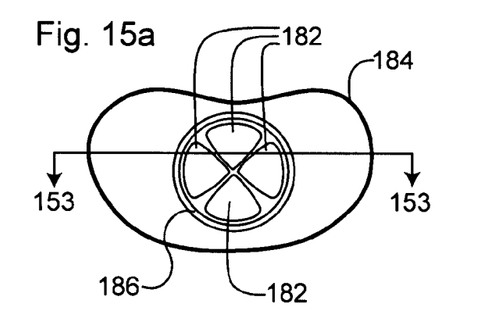
FIG. 15A shows a top view of an end plate from the disc depicted in FIG. 12.
Figure 15B:
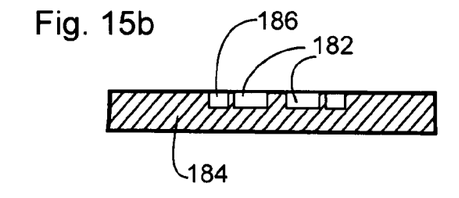
FIG. 15B shows a cross section of the end plate shown in FIG. 15A.

FIG. 15A provides a top view of lower end plate (184). This view further shows the openings (182) into which core segments (174) are situated after assembly of the prosthetic disc (170). FIG. 15B provides a cross section of the lower end plate (184) and also shows the depth of openings (182) into which core segments (174) are placed. FIG. 15A further shows a groove (186) into which a portion of bellows member (178) is placed. The depth of groove (186) may be readily seen in the cross-sectional view provided in FIG. 15B.

Figure 16:
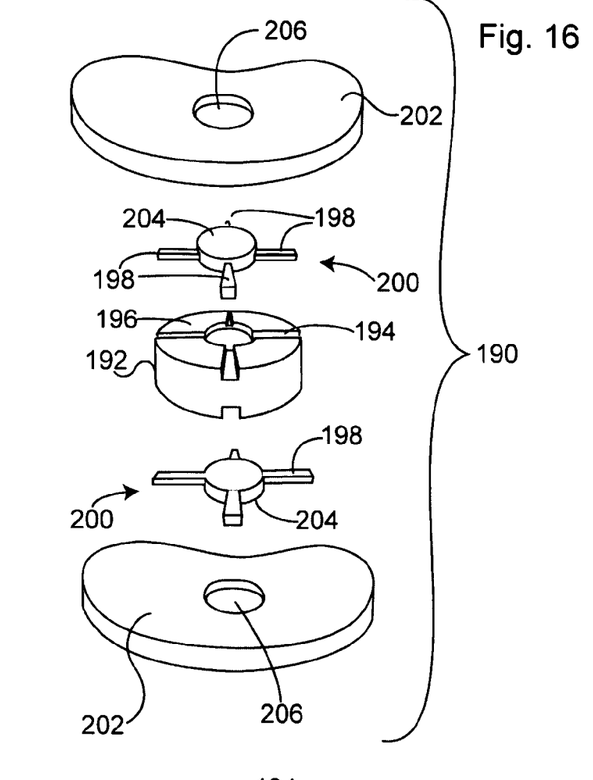
FIG. 16 shows exploded perspective view of another variation of our prosthetic disc.

FIG. 16 shows an exploded view of another variation of our prosthetic disc assembly (190). Disc assembly (190) includes a compressible core element (192) having of radial slots or grooves (194). Grooves (194) separate each of the upper and lower faces of core element (192) into a number of lands (196) that serve as extensions into the open regions between the arms (198) of spider (200). Each of the two spiders (200) are fixedly attached to their respective end plates (202) as by welding.

The buttons or extensions (204) of spiders (202) extend into openings (206) and may be welded to end plates (202) from that exterior surface. In this variation, the arms (198) are not themselves fixedly attached to the adjoining surface of end plates (202). This allows arms (198) to act as spring members during torsion or twisting of disc assembly (190). The compliance of compressible core element (192) and the physical interaction of arms (198) acting as cantilever springs and provides a twisting force versus resistance relationship that is steadily progressive during the first few degrees of movement and is readily self-restoring.

Figure 17A:
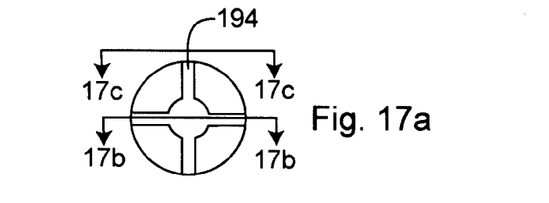
FIG. 17A shows a top view of a compressible core element found in the disc shown in FIG. 16.
Figure 17B:
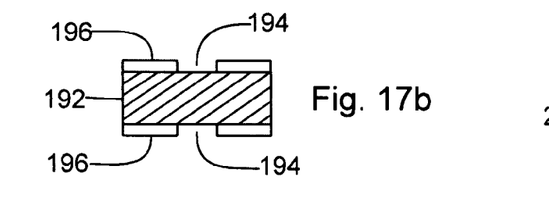
FIG. 17B shows a side view, cross section of the core element shown in FIG. 17A.
Figure 17C:
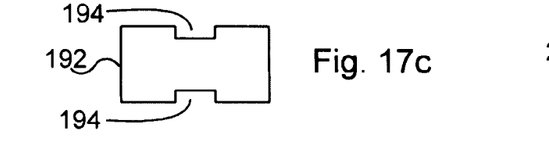
FIG. 17C provides a cross section of the core element shown in FIG. 17A.

FIG. 17A provides a top view of compressible core member (192). Also visible are grooves (194). FIG. 17B provides a cross section side view of compressible core member (192). The lands (196) formed and defined by grooves (194) may also be seen. FIG. 17C provides a side view of compressible core member (192). Grooves (194) on both the upper and lower surfaces of core member (192) may be seen.

Figure 18A:
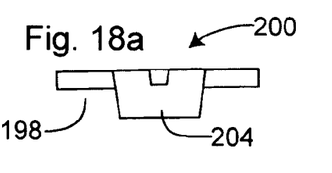
FIG. 18A shows a side view of a spider element found in the prosthetic disc portrayed in FIG. 16.
Figure 18B:
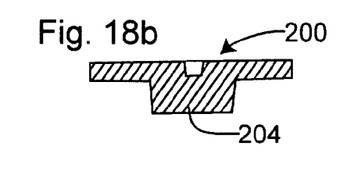
FIG. 18B shows a side view cross-section of the spider shown in FIG. 18A.

FIG. 18A is a side view of one of the spiders (200) having arms (198) and extension or weld button (204). FIG. 18B provides a cross-sectional side view of the spider (200) shown in FIG. 18A.

Figure 19:
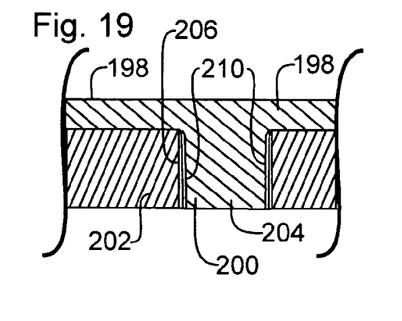
FIG. 19 shows a partial cross-section of the intersection between the spider member and the end plate showing weld positioning between those two elements in the prosthetic disc shown in FIG. 16.

FIG. 19 shows a spider member (200) affixed to an end plate (202) by welds (210) and the contiguous areas of extension (204) and the wall of opening (206) in end plate (202). Note that there are no welds in the contact area between spider arm (198) and end plate (202). It should be apparent that this weld region (210) affixes the spider (200) to the end plate (202) and yet allows arms (198) to flex.

Figure 20:
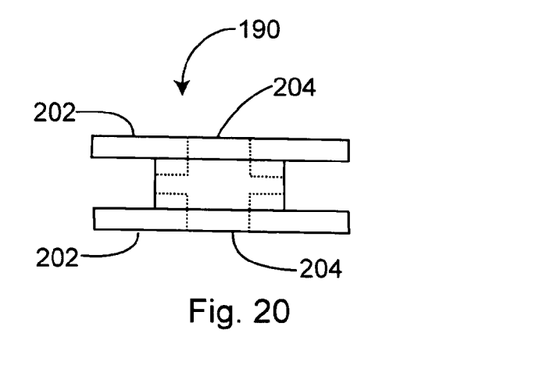
FIG. 20 shows a side view of the FIG. 16 variation of our prosthetic disc.

FIG. 20 shows a side view of the assembled disc assembly (190). Also shown in FIG. 20 is the extension of weld button (204) though the end plates (202). As has been the case with discussions of many of the other variations here, the disc assembly (190) shown in FIGS. 16 and 20 may be a subassembly of a complete prosthetic disc in the sense that many designers would also include a stress member or members. Examples of such stress members will be discussed elsewhere.

Figure 21:
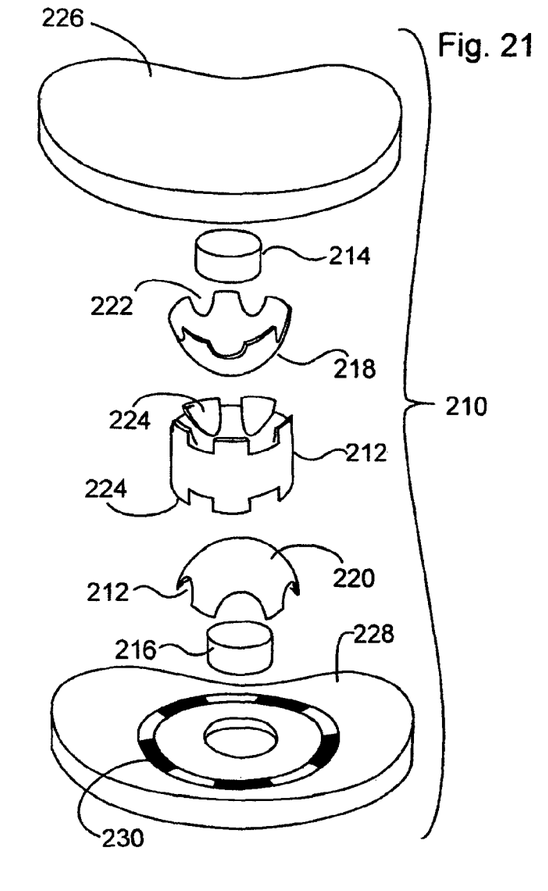
FIG. 21 shows an exploded perspective view of another variation of our prosthetic disc.

FIG. 21 provides an exploded view of another variation of our prosthetic disc assembly (210). Disc assembly (210)

includes a central compressible core member (212), and two optional support compressible core members (214, 216), a pair of opposed spherical springs (218,220), each with peripheral cutouts (222) that mesh with protrusions (224) extending from central compressible core member (212), and end plates (226, 228) having a slot region (230) that limits the rotation of opposing spherical springs (218, 220) during axial twisting of the disc assembly (210) between end plates (226 228).

Figure 22:
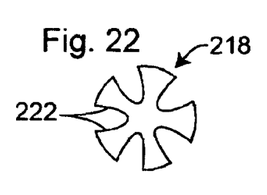
FIG. 22 shows a top view of the spherical spring utilized in the disc shown in FIG. 21.

FIG. 22 shows a top view of one of the spherical springs (218) with cutouts or slots (222) extending inwardly from periphery of spring (218). The size of the cutouts (222) may be adjusted, both in width and in length, to vary the spring rate of spring (218).

Figure 23:
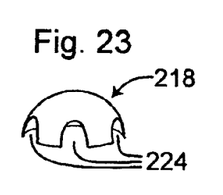
FIG. 23 shows a side view of the spherical spring shown in FIG. 22.

FIG. 23 provides a side view of one of the spherical springs (218) and the peripheral slots or cutouts (222). These springs may be shapes other than spherical. For instance, they may be provided with an oval footprint in the adjacent end plate. They may be non-spherical in shape, for instance, ellipsoidal. Further, the two springs (e.g., 218, 220) need not be of the same shape. If spherical, the two opposing springs need not have the same radius.

Figure 24:
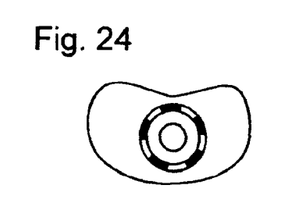
FIG. 24 shows a top view of an end plate found in the prosthetic disc shown in FIG. 21.

FIG. 24 shows a top view of one of the end plates (228) with a, slot region (230) that contains a number of openings (232) for receiving the bottom end of one of the springs, such openings (218, 220) being separated by stop regions (234) that are not open and consequently do not receive the bottom of such springs. Stop regions (234) are sized to prevent or to control the axial rotation of the springs (218, 220) when those springs are inserted in that end plate (228).

Figure 25:
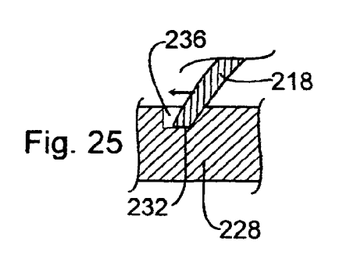
FIG. 25 is a cross sectional, blow up view of the intersection between the spherical spring and the end plate variation shown in FIG. 21.

FIG. 25 is a side view of the foot of spring (218) inserted into one of the openings (32) in the slot region (230) of end plate (228). It should be noted that opening (232) includes a region of clearance (236) allowing spring (218) to flex radially during usage.

Figure 26:
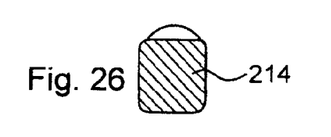
FIG. 26 shows a cross-sectional side view of the supporting core member as used in the disc shown in FIG. 21.

FIG. 26 shows a side view of one of the optional compressible support core members (e.g., 214, 216). In general, such a support core member provides additional control in the sense of tailorability, to the overall gross compressibility of the prosthetic disc (210) and to the rate (i.e., gross compressibility) at which the disc assembly (210) is compressed as a function of applied force (gross compression vs applied force).

Figure 27A:
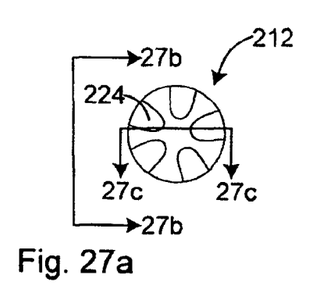
FIG. 27A shows a top view of the central core member used in the disc assembly shown in FIG. 21.
Figure 27B:
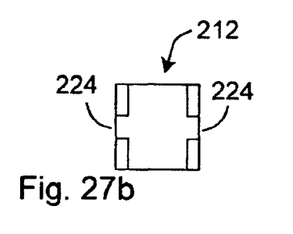
FIG. 27B shows a side view of the core member.
Figure 27C:
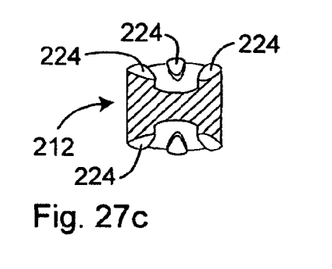
FIG. 27C shows a side view, cross-section of the core member.

FIGS. 27A, 27B, and 27C show, respectively, a top view, a side view, and a cross-sectional side view of the central compressible core member (212).

FIG. 27A shows a top view of one variation of a central compressible core member (212) and protuberances and extend into spring members (218, 220) when the prosthetic disc assembly (210) is assembled. FIG. 27B is a side view of central compressible core member (212) with its attendant extensions or protuberances (224). FIG. 27C shows a cutaway side view of a central compressible core member (212) and its extensions (224). Note that the shape of the depressions on each opposing side of the central core member (212) conforms to the shape of the spherical spring member (218, 220).

Figure 28:
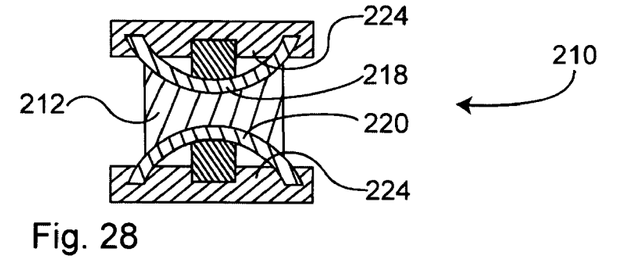
FIG. 28 shows a side view cross-section of the disc assembly of the type shown in FIG. 21.

FIG. 28 provides a cross-sectional side view of the assembled prosthetic disc assembly (210) shown in FIG. 21. A first spring (218) and a second spring (220) may be seen fitted within the opposing depressed areas within central core member (212). The protuberances (224) may be seen extending up into the openings found in those spring members (218, 220) to prevent or to limit rotation of a central core member (212) with respect to those spring members (218, 220). Further FIG. 28 shows placement of spring members (218, 220)

FIGS. 29A to 31 show a variation of the prosthetic disc shown in FIG. 21 and its components.

Figure 29A:
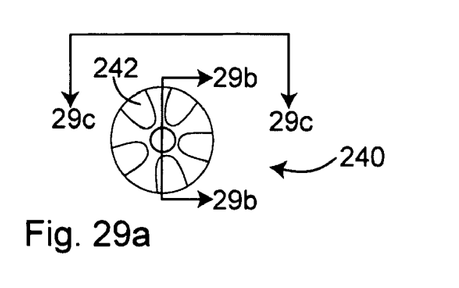
FIG. 29A shows a top view of another variation of elastic core member that may be used in the prosthetic disc design shown in FIG. 21.

FIG. 29A shows the top view of a compressible core element (240) and integrates the end buttons of the FIG. 28 component into a single unit. The extensions (242) of core element (240) also extend though the central springs (244, 246 in FIG. 31) to contact the opposing end plates (248, 250 in FIG. 31). The button extensions (252, 254) extend through the openings (256) in the central springs (244, 246) to and then into the openings (260, 262) in the end plates (250, 254).

Figure 29B:
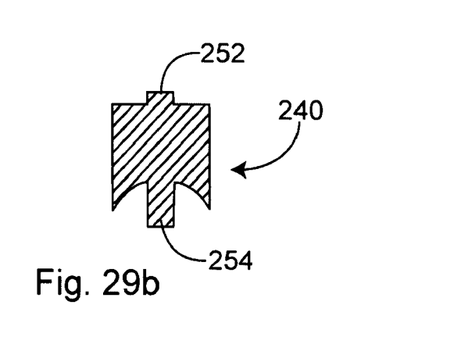
FIG. 29B shows a side view cross-section of that elastic core member.
Figure 29C:
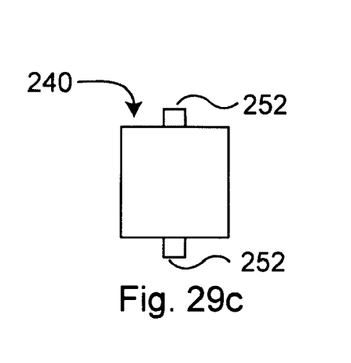
FIG. 29C shows a side view of that core member.

FIG. 29B provides a cross section of the core element (240) shown in FIG. 29A and further shows the button extensions (252, 254). FIG. 29C provides a side view of the core element (240) shown in FIG. 29A.

Figure 30A:
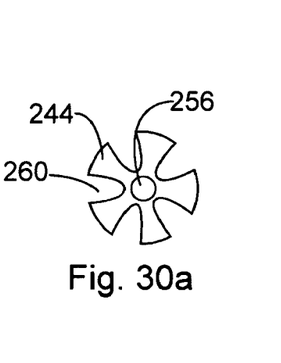
FIGS. 30A and 30B show, respectively a top view and a side view of a spherical spring suitable for use with the core member shown in FIGS. 29A to 29C.
Figure 30B:
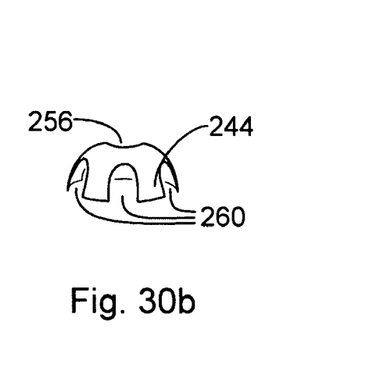

FIGS. 30A and 30B show, respectively, a top view, and a side view of one of the spherical springs (244). The spherical spring (244) includes a number of notches (260) extending from the periphery of the spring (244). The opening (256) in the top of the spring (244) may also be seen. The springs (244, 246) may be substantially similar to the springs (218, 220) shown with regard to another variation discussed herein (210 in FIG. 21) with the exception that springs (244, 246) include a top opening (256).

Figure 31:
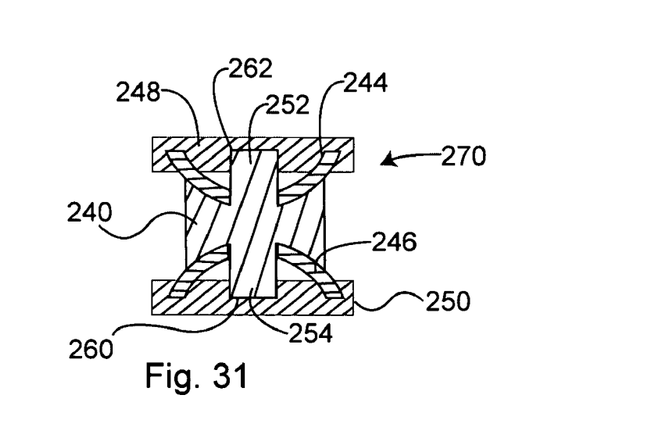
FIG. 31 provides a cross-sectional side view of the assembled prosthetic disc using the core member shown in FIGS. 29A to 29C and the spring shown in FIGS. 30A and 30B.

FIG. 31 provides a side, cross-sectional view of this variation of our assembled prosthetic disc (270) using the core element (240). The two springs (244, 246) fit within the core element (240) and the spring peripheries inserted into the two end plates (248, 250). The button extensions (252, 254) extend into the end plates (248, 250).

Figure 32:
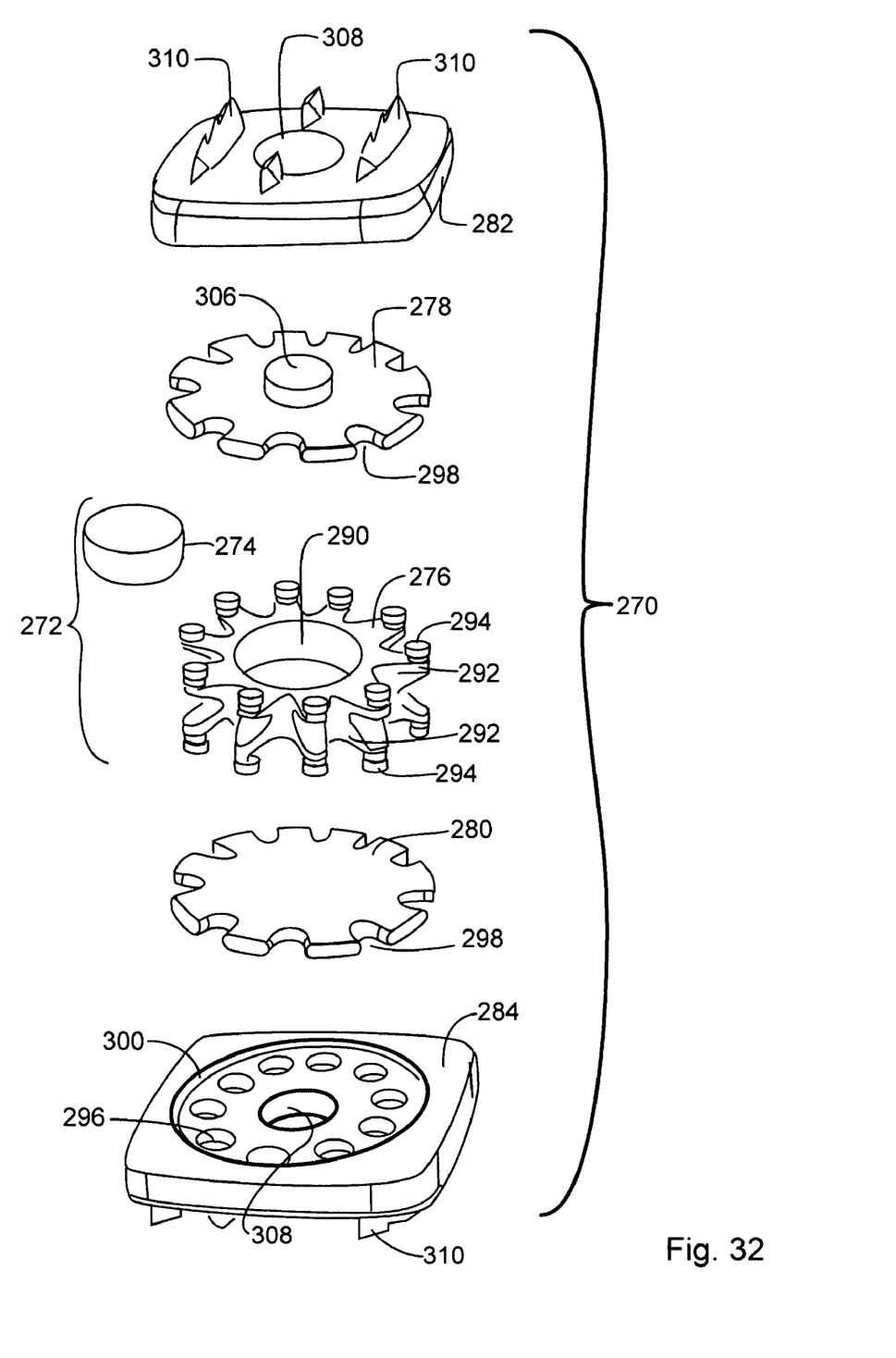
FIG. 32 shows an exploded view of another variation of our prosthetic disc.
Figure 33:
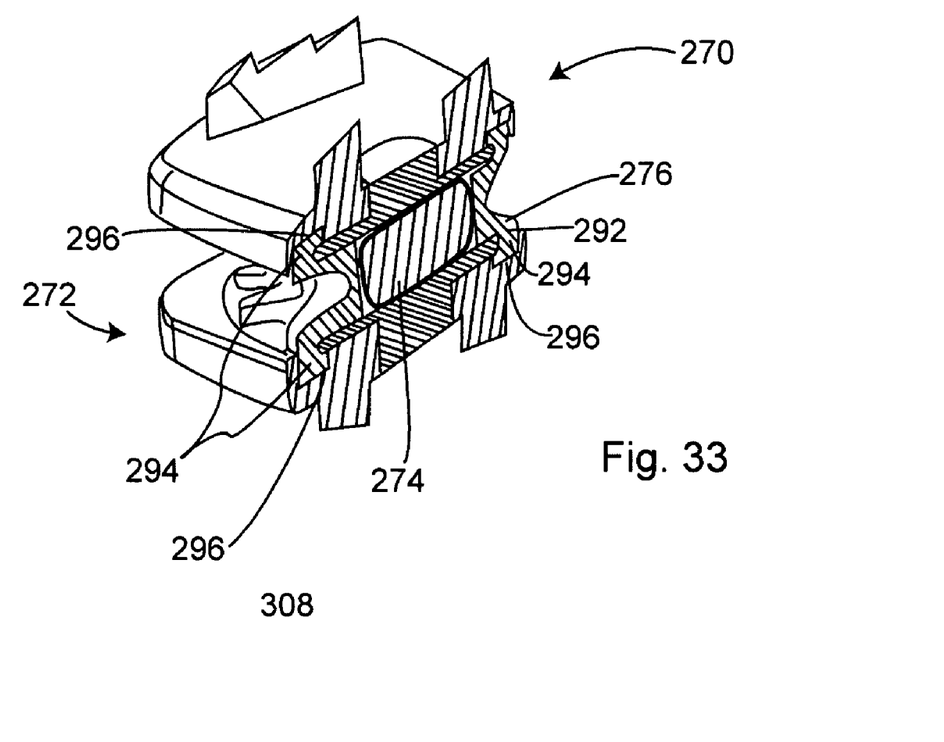
FIG. 33 shows a perspective, cross-sectional view of the assembled disc portrayed in FIG. 32.
Figure 34:
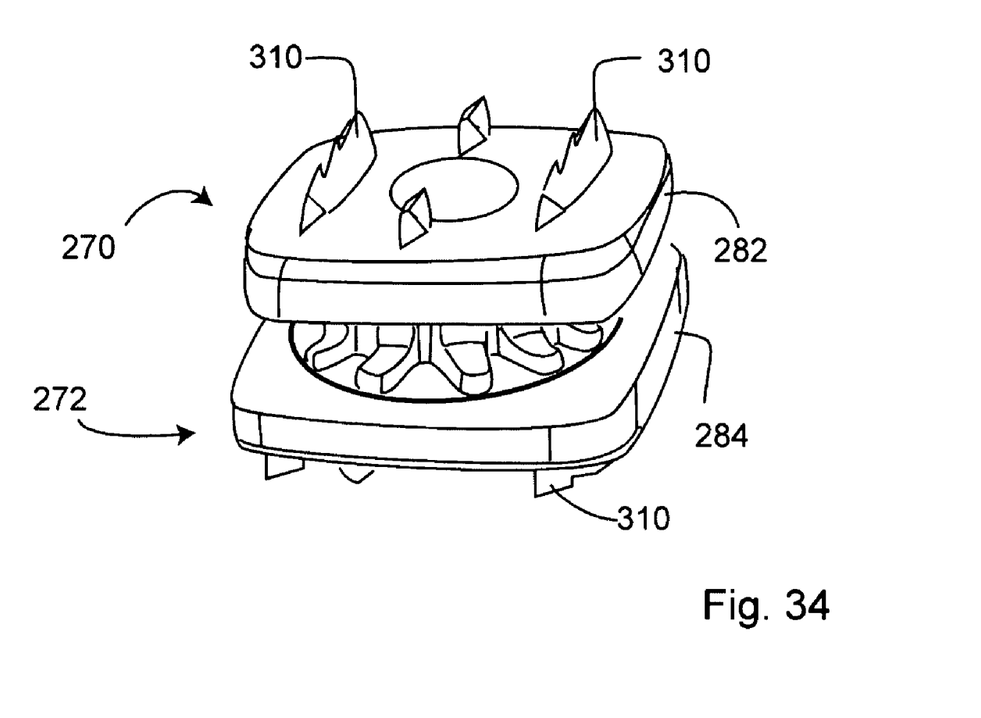
FIG. 34 shows a perspective view of the assembled disc as shown in FIG. 32.

FIGS. 32, 33, and 34 provide, respectively, an exploded view, a perspective cross-sectional view, and a perspective front view of another variation (270) of our prosthetic disc. This prosthetic disc (270) includes a composite compressible core (272) comprising a central core element (274) and a spider core component (276). The compressible, central spider core element (276) interfits or interlocks with the two inner end plates (278, 280). Further, those inner end plates (278, 280) in turn integrate into and are welded to their respective outer end plates (282 284).

Central core element (274) desirably approximates the physical parameters of the native *nucleus pulposa* and may comprise, for instance, a neat hydrogel, mixed hydrogel, an envelope containing a appropriate hydrogel, gel, or other fluids. The central core element (274) fits within the opening (290) within spider core element (276).

Spider core element (276) further comprises a member of (or multiplicity of) arms or fingers (292) having buttons (294) at the end of each of those fingers (292) that fit in, within, and through the peripheral notches or openings (298) in the two inner end plates (278, 280). The buttons (294) further fit into the openings (296) found on the respective inner surfaces of the outer end plates (282, 284) when the inner end plates (278, 280) are fitted in place within the outer end plates (282, 284). The inner end plates (278, 280) fit within the circular ridges (300) found within outer end plates (282, 284).

As noted elsewhere, the core may comprise an elastomeric material desirably having a compressibility of 737 N/mm +/−885 N/mm, In particular, the compressible core member in this variation and the others discussed herein, may comprise a thermoplastic elastomer (TPE) as a polycarbonate-urethane TPE having, e.g., a Shore value of 50 D to 60 D, e.g. 55 D. An example of such a material is the commercially available TPE, Bionate. Shore hardness is often used to specify flexibility or flexural modulus for elastomers.

We have had success with core members comprising TPE that are compression molded at a moderate temperature from an extruded plug of the material. For instance, with the polycarbonate-urethane TPE mentioned above, a selected amount of the polymer is introduced into a closed mold upon which a substantial pressure may be applied, while heat is applied. The TPE amount is selected to produce a compression member having a specific height. The pressure is applied for 8-15 hours at a temperature of 70°-90° C., typically about 12 hours at 80° C.

Other examples of suitable representative elastomeric materials include silicone, polyurethanes, or polyester (e g., Hytrel®).

Compliant polyurethane elastomers are discussed generally in, M. Szycher, J. Biomater. Appl. "Biostability of polyurethane elastomers: a critical review", 3(2):297 402 (1988), A. Coury, et al., "Factors and interactions affecting the performance of polyurethane elastomers in medical devices", J. Biomater. Appl. 3(2):130 179 (1988); and Pavlova M, et al., "Biocompatible and biodegradable polyurethane polymers", Biomaterials 14(13):1024 1029 (1993). Examples of suitable polyurethane elastomers included aliphatic polyurethanes, segmented polyurethanes, hydrophilic polyurethanes, polyether-urethane, polycarbonate-urethane and silicone-polyether-urethane.

Other suitable elastomers include various polysiloxanes (or silicones), copolymers of silicone and polyurethane, polyolefins, thermoplastic elastomers (TPE's) such as atactic polypropylene, block copolymers of styrene and butadiene (e.g., SBS rubbers), polyisobutylene, and polyisoprene, neoprene, polynitriles, artificial rubbers such as produced from copolymers produced of 1-hexene and 5-methyl-1,4-hexadiene.

In sum, the spider core element (276) provides for the transmission of and distribution of complicated, multi-directional forces, variously push and pull side to side, flexion-extension, and rotation from one end plate the other.

The inner end plates (278, 280) additionally are shown to have welding extensions (306) that fit within passageways (308) found in outer end plates (282, 284). The welding extensions (306) typically would be welded in place from the outside surfaces of outer end plates (282, 284).

Also shown in FIG. 32 are optional barbed keels (310) that may be used to affix the assembled prosthetic disc (270) to adjacent vertebrae in the spine when this prosthetic disc is inserted in the space between to such vertebrae. Other components (integrated into end plates or not) suitable for affixing this prosthetic disc appropriately to those adjacent discs are discussed below.

FIG. 33 shows a cutaway of this version of the prosthetic, disc and illustrates with clarity the relationships amongst the various components in this disc variation. Central core component (274) is seen situated within spider core component (276). Of special interest is the recessed placement of the buttons (294) at the ends of arms (292) and within the openings (296) in inner end plates (278, 280). The buttons (294) provide a physical link between the composite core (272) by interlocking with the respective inner and outer end plates.

FIG. 34 provides a perspective view of the assembled prosthetic disc (270). The upper end plate (282) and lower end plate (284) with affixed keel shaped components (310) are visible. This view is from the end of the disc assembly (207) as would be seen looking from the back of the patient through the spine. The barbed keels (310) in this variation would be a buried in vertebral bone. The flexible compressible central core assembly (272) may be seen separating the two outer end plates (282, 284).

Figure 35:
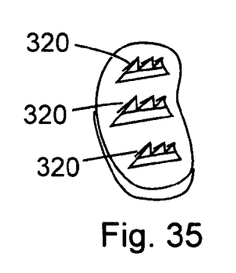
FIGS. 35 to 37 show examples of various components or means suitable for affixing our prosthetic discs to vertebral bone.
Figure 36:
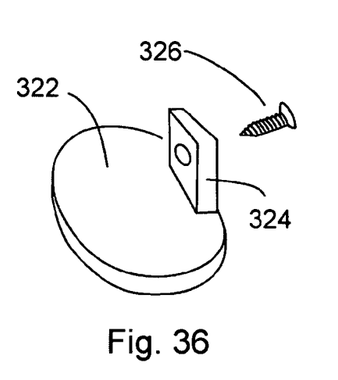
Figure 37:
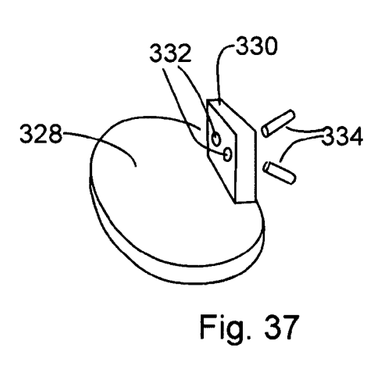

FIGS. 35, 36, and 37 show various components or devices useful affixing our prosthetic spinal disc to a spine.

FIG. 35 shows a barbed keel (320) that may be integrated into the end plates shown herein. These barbed keels (320) may be sized to fit in keel tracks or slots that are cut or chiseled into cortical bone of the spine. The keels need not be very tall to allow immediate and acute fixation by means of a press fit into the slots or keel tracks. For instance, we have found that keel heights of approximately 1.8 mm are quite effective for immediate and long-term fixation.

FIG. 36 shows an end plate (322) having an integral securing tab (324). A bone screw (326) is used to secure the implant into the spinal bone.

FIG. 37 shows still another variation in which end plate (328) is equipped with an integral tab (330) having canted openings (332) allowing the insertion of pins (334) to forms a "V" behind the tab (330) in previously prepared holes in the cortical bone of the vertebral body adjacent end plate (328) and thereby fix the prosthetic disc to the spine.

Such components may be added by the designer, as independent or integrated components, to a specific design made according to our teachings here to affix the finally designed prosthetic disc to spinal vertebrae.

Figure 38A:
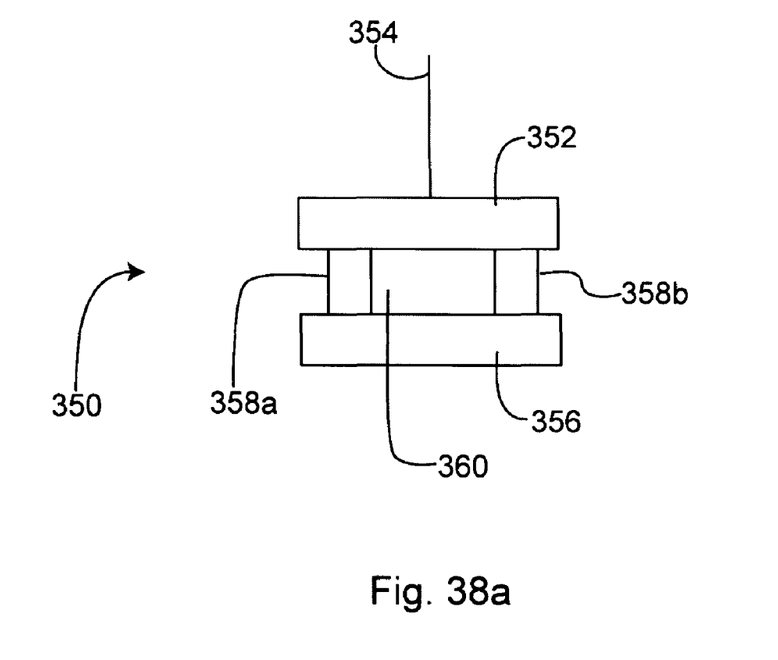
FIGS. 38A and 38B show, in a schematic fashion, the transfer of force between endplates and stress members as a force or moment is applied to one of the endplates.
Figure 38B:
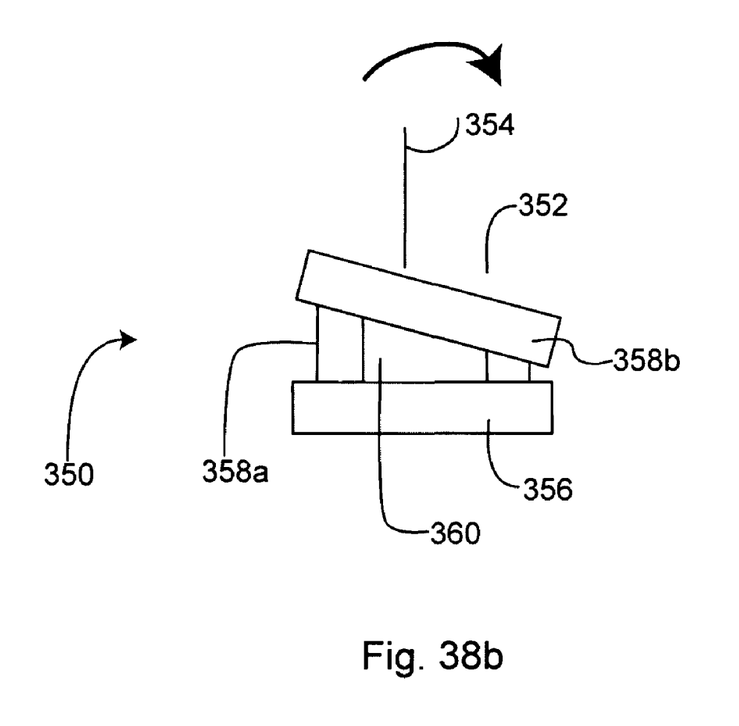
Figure 39:
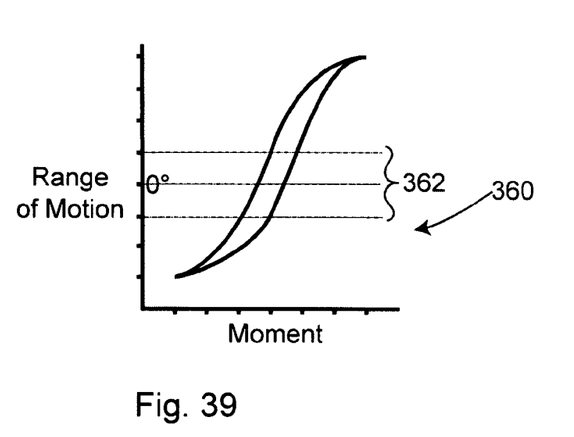
FIG. 39 is a graph of a typical range of motion response as a force or moment is applied to an end plate as is depicted in FIG. 338A and 38B.

FIGS. 38A and 38B show, in a schematic fashion, the ways in which application of the force to an end member results in motion of that member and the concomitant effects upon what we have denominated a "stress member" and the compressible core member. FIG. 39, in turn, provides a graphic representation of the movement-force relationship and in particular shows both the nonlinearity of the relationship and the presence of a "neutral zone" generally centered in that motion. The form of the relationship, as depicted in FIG. 39, generally is the same in each of flexion-extension, side-to-side motion, and rotational or twisting motion.

FIG. 39A schematically shows one of our prosthetic discs (350) having upper end plate (352) with an arbitrary pole (354) depicting a defined axis of that upper end plate (352), and further having a lower end plate (356), schematic stress members or components of the stress members (358a, 358b) and a core element (360). A specific prosthetic disc design may have more than the two stress members (or stress member components) as shown in FIG. 38A, but the remainder of the stress members have been removed from this depiction for the purpose of explanation. In this schematic assembly, the stress members (358) are fixedly attached to the significantly stiffer upper end member (352) and a lower end member (356).

As seen in FIG. 35B, as a force is applied to upper end member (352), from left to right, some portion of the core member (360) is compressed, the left stress member (358a) is stretched and the other stress member (358b) in the right of the depiction is relaxed or, at least, the amount of stress on the left stress member (358a) is increased as the member is stretched and the amount of stress on the other stress member (358b) in the right of the depiction is lessened as the stress member is relaxed.

FIG. 39 shows a graph (360) of the generalized desired relationship of the rotatory motions exhibited by our device when subjected to various forces or moments. The hysteresis exhibited in graph (360) also shows the self-restoring (or self-centering) feature of the prosthetic disc. The hysteresis provides for a "zone" (362) in which the prosthetic disc allows a range of motion of a few degrees without the application of substantial force. In a natural disc, the extent of the neutral zone in the three noted motions, i.e., flexion-extension, side-to-side, and axial twisting, changes with such variables as: the location of the disc in the spine, age, disease state, and to a lesser extent, time of day and level of health. Cervical discs have an extensive neutral zone (e.g., +4° to −2.5° in flexion-extension) and ultimate range of motion (ROM) limits (e.g., 10° to 13° in flexion-extension; 8° to 10° in lateral movement; and 8° to 10° in axial rotation) in each of the noted motions. Lumbar discs generally have a less extensive neutral zone and ROM limits.

As discussed elsewhere, addition or inclusion of a stress member such as shown schematically in FIGS. 38A and 38B may be desirable. The variation shown in FIG. 32 et seq includes the stress member function in the spider core member and consequently an added stress member may not be desirable. But inclusion of such a stress member in the other depicted variations may be desired as a component of a functional disc if the designer desires a closer approach to biomechanical similarity is desired.

Figure 40:
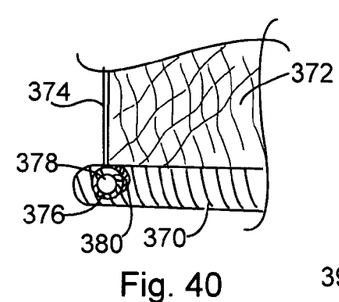
FIGS. 40 to 42 show examples of stress members suitable for use: in our prosthetic disc.
Figure 41:
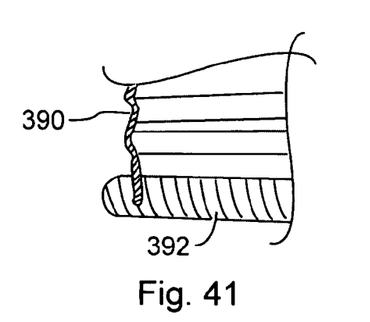
Figure 42:
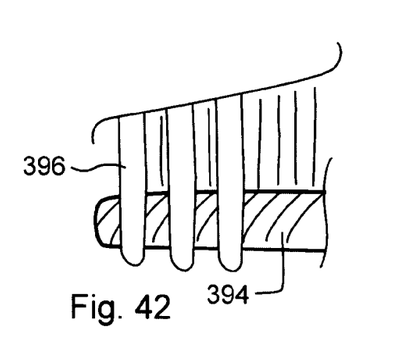

FIGS. 40-42 provide examples of stress members that may be added to a disc design as desired.

FIG. 40 shows a cross section of a portion of an end plate (370) and an elastic core component (372). A stress member (374) comprising, e.g., a polymeric membrane containing a fabric is anchored in a groove (376) by wrapping the fabric around a wire (379) and capturing that wire (378) and membrane using an interference member (380) in the groove (376). The stress member (374) is affixed to the end plate and will transfer forces as generally shown in FIGS. 38A and 38B. The stress member may encircle the disc if so desired.

FIG. 41 shows another cross section of a stress member (390) embedded in an end plate (392). The depicted stress member (390) is shown to be a bellows and may comprise a polymeric material or metal. The method of affixing the stress member (390) to the end plate (392) will depend upon the materials chosen for the stress member (390) and end plate (392).

FIG. 42 shows a partial cross section of an end plate (394) and a number of fibers (396) passing through openings in the end plate (394). The fibers (396) are secured by any of a variety of methods including simply tying them to the end plate (394) or by gluing them to the end plate (394). The fibers collectively act as the stress member.

I claim as my invention:

1. A prosthetic intervertebral disc comprising:
    a.) a first end plate assembly affixable to a vertebral bone in a spine, comprising:
        i.) a first outer end plate operable to cooperate with a first inner end plate to interlock with a compressible core member having a plurality of core member flexible arms each terminating in a button, each said button insertable into a first or second outer end plate opening, the first outer end plate having a plurality of openings, each said opening operable to accept a button terminating a core member flexible arm, the first outer end plate having
            A.) an outer side, and
            B.) an inner side, and
        ii.) the first inner end plate having
            A.) an outer side configured to be positioned adjacent the inner side of the first outer end plate, and
            B.) an inner side,
    b.) a second end plate assembly affixable to an adjacent vertebral bone in a spine comprising:
        i.) a second outer end plate operable to cooperate with a second inner end plate to interlock with the compressible core member having a plurality of core member flexible arms each terminating in a button, the second outer end plate having a plurality of openings, each said opening operable to accept a button terminating a core member flexible arm, the second outer end plate having
            A.) an outer side, and
            B.) an inner side, and
        ii.) the second inner end plate having
            A.) an outer side configured to be positioned adjacent the inner side of the second outer end plate, and
            B.) an inner side, and
    c.) the polymeric compressible core member having an axis, said axis also passing through the first end plate assembly and the second end plate assembly, the core member having a central region through which the axis passes, the core member including a plurality of flexible core member arms extending from the central region and each terminating in a button, each said button insertable into a first or second outer end plate opening, and the compressible core member being operational to interlock with said first and second end plate assemblies such that when a twisting force is imparted to one of said end plate assemblies about that axis, the compressible core member transmits the twisting force from that end plate assembly to the other end plate assembly.

2. The prosthetic intervertebral disc of claim 1 wherein:
    a.) the first outer end plate has a passageway extending from the inner side of the first outer end plate to the outer side of the first outer end plate,
    b.) the first inner end plate includes an extension configured for passage from the inner side of the first outer end plate through the first outer end plate passageway and for fixation to the outer side of the of the first outer end plate,
    c.) the second outer end plate has a passageway extending from the inner side of the second outer end plate to the outer side of the second outer end plate, and
    d.) the second inner end plate includes an extension configured for passage from the inner side of the second outer end plate through the second outer end plate passageway and for fixation to the outer side of the of the second outer end plate.

3. The prosthetic intervertebral disc of claim 1 wherein the core member includes a central passageway including the axis and operable to accept a flexible cylindrical central core element extending from the first inner end plate to the second inner end plate and wherein the core member further comprises the cylindrical central core element.

4. The prosthetic intervertebral disc of claim 3 wherein the core member comprises a thermoplastic elastomer or silicone.

5. The prosthetic intervertebral disc of claim 2 wherein the core member includes a central passageway including the axis and operable to accept a flexible cylindrical central core element extending from the first inner end plate to the second inner end plate and wherein the core member further comprises the cylindrical central core element.

6. The prosthetic intervertebral disc of claim 5 wherein the core member comprises a thermoplastic elastomer or silicone and wherein the flexible cylindrical central core element comprises a thermoplastic elastomer or silicone.

7. The prosthetic intervertebral disc of claim 5 wherein the core member comprises a thermoplastic elastomer or silicone and wherein the flexible cylindrical central core element comprises a hydrogel.

8. The prosthetic intervertebral disc of claim 1 wherein the core member comprises a thermoplastic elastomer or silicone.

9. The prosthetic intervertebral disc of claim 1 further comprising fixation elements for directly affixing the first and second end plates to vertebral bone.

10. A prosthetic intervertebral disc comprising:
a.) a first end plate assembly affixable to a vertebral bone in a spine, comprising:
   i.) a first outer end plate operable to cooperate with a first inner end plate to interlock with a compressible core member having a plurality of core member flexible arms each terminating in a button, each said button insertable into a first or second outer end plate opening, the first outer end plate having a plurality of openings, each said opening operable to accept a button terminating a core member flexible arm, the first outer end plate having
      A.) an outer side, and
      B.) an inner side, and
      C.) a passageway extending from the inner side of the first outer end plate to the outer side of the first outer end plate, and
   ii.) the first inner end plate having
      A.) an outer side configured to be positioned adjacent the inner side of the first outer end plate, and
      B.) an inner side, and
      C.) an extension configured for passage from the inner side of the first outer end plate through the first outer end plate passageway and for fixation to the outer side of the of the first outer end plate, and
b.) a second end plate assembly affixable to an adjacent vertebral bone in a spine comprising:
   i.) a second outer end plate operable to cooperate with a second inner end plate to interlock with the compressible core member having a plurality of core member flexible arms each terminating in a button, the second outer end plate having a plurality of openings, each said opening operable to accept a button terminating a core member flexible arm, the second outer end plate having
      A.) an outer side, and
      B.) an inner side, and
      C.) a passageway extending from the inner side of the second outer end plate to the outer side of the second outer end plate, and
   ii.) the second inner end plate having
      A.) an outer side configured to be positioned adjacent the inner side of the second outer end plate, and
      B.) an inner side, and
      C.) an extension configured for passage from the inner side of the second outer end plate through the second outer end plate passageway and for fixation to the outer side of the of the second outer end plate, and
c.) the polymeric compressible core member having an axis, said axis also passing through the first end plate assembly and the second end plate assembly, the core member having a central region through which the axis passes, the core member including a plurality of flexible core member arms extending from the central region and each terminating in a button, each said button insertable into a first or second outer end plate opening, and the compressible core member being operational to interlock with said first and second end plate assemblies such that when a twisting force is imparted to one of said end plate assemblies about that axis, the compressible core member transmits the twisting force from that end plate assembly to the other end plate assembly.

11. The prosthetic intervertebral disc of claim 10 wherein the core member includes a central passageway including the axis and operable to accept a flexible cylindrical central core element extending from the first inner end plate to the second inner end plate and wherein the core member further comprises the cylindrical central core element.

12. The prosthetic intervertebral disc of claim 11 wherein the core member comprises a thermoplastic elastomer or silicone and wherein the flexible cylindrical central core element comprises a thermoplastic elastomer or silicone.

13. The prosthetic intervertebral disc of claim 11 wherein the core member comprises a thermoplastic elastomer or silicone and wherein the flexible cylindrical central core element comprises a hydrogel.

14. The prosthetic intervertebral disc of claim 10 wherein the core member comprises a thermoplastic elastomer or silicone.

15. The prosthetic intervertebral disc of claim 10 further comprising fixation elements for directly affixing the first and second end plates to vertebral bone.

16. A prosthetic intervertebral disc comprising:
a.) a first end plate assembly affixable to a vertebral bone in a spine, comprising:
   i.) a first outer end plate operable to cooperate with a first inner end plate to interlock with a compressible core member having a plurality of core member flexible arms each terminating in a button, each said button insertable into a first or second outer end plate opening, the first outer end plate having a plurality of openings, each said opening operable to accept a button terminating a core member flexible arm, the first outer end plate having
      A.) an outer side, and
      B.) an inner side, and
   ii.) the first inner end plate having
      A.) an outer side configured to be positioned adjacent the inner side of the first outer end plate, and
      B.) an inner side,
b.) a second end plate assembly affixable to an adjacent vertebral bone in a spine comprising:
   i.) a second outer end plate operable to cooperate with a second inner end plate to interlock with the compressible core member having a plurality of core member flexible arms each terminating in a button, the second outer end plate having a plurality of openings, each said opening operable to accept a button terminating a core member flexible arm, the second outer end plate having
      A.) an outer side, and
      B.) an inner side, and
   ii.) the second inner end plate having
      A.) an outer side configured to be positioned adjacent the inner side of the second outer end plate, and
      B.) an inner side, and
c.) the polymeric compressible core member having an axis, said axis also passing through the first end plate assembly and the second end plate assembly, the core member having a central region through which the axis passes, having a central passageway including the axis, the central passageway operable to accept a flexible cylindrical central core element extending from the first inner end plate to the second inner end plate and wherein the core member further comprises the cylindrical central core element and a plurality of flexible core member arms extending from the central region and each terminating in a button, each said button insertable into a first or second outer end plate opening, and the compressible core member being operational to interlock with said first and second end plate assemblies such that when a twisting force is imparted to one of said end plate assemblies about that axis, the compressible core member transmits the twisting force from that end plate assembly to the other end plate assembly.

17. The prosthetic intervertebral disc of claim 16 wherein:
a.) the first outer end plate has a passageway extending from the inner side of the first outer end plate to the outer side of the first outer end plate,
b.) the first inner end plate includes an extension configured for passage from the inner side of the first outer end plate through the first outer end plate passageway and for fixation to the outer side of the of the first outer end plate,
c.) the second outer end plate has a passageway extending from the inner side of the second outer end plate to the outer side of the second outer end plate, and
d.) the second inner end plate includes an extension configured for passage from the inner side of the second outer end plate through the second outer end plate passageway and for fixation to the outer side of the of the second outer end plate.

18. The prosthetic intervertebral disc of claim 17 wherein the core member comprises a thermoplastic elastomer or silicone.

19. The prosthetic intervertebral disc of claim 16 wherein the core member comprises a thermoplastic elastomer or silicone.

20. The prosthetic intervertebral disc of claim 16 wherein the core member comprises a thermoplastic elastomer or silicone and wherein the flexible cylindrical central core element comprises a thermoplastic elastomer or silicone.

21. The prosthetic intervertebral disc of claim 16 wherein the core member comprises a thermoplastic elastomer or silicone and wherein the flexible cylindrical central core element comprises a hydrogel.

22. The prosthetic intervertebral disc of claim 16 further comprising fixation elements for directly affixing the first and second end plates to vertebral bone.

* * * * *